(12) United States Patent
Ten Dam et al.

(10) Patent No.: US 10,654,764 B2
(45) Date of Patent: May 19, 2020

(54) PROCESS FOR THE PRODUCTION OF AN ALKYLATED AROMATIC PRODUCT

(71) Applicant: JOHNSON MATTHEY PUBLIC LIMITED COMPANY, London (GB)

(72) Inventors: Jeroen Ten Dam, Voorburg (NL); Lockhart Edward Horsburgh, Billingham (GB); Michael John Watson, Billingham (GB)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 16/331,265

(22) PCT Filed: Sep. 12, 2017

(86) PCT No.: PCT/GB2017/052670
§ 371 (c)(1),
(2) Date: Mar. 7, 2019

(87) PCT Pub. No.: WO2018/051070
PCT Pub. Date: Mar. 22, 2018

(65) Prior Publication Data
US 2019/0218157 A1    Jul. 18, 2019

(30) Foreign Application Priority Data

Sep. 14, 2016 (GB) .................... 1615628.3

(51) Int. Cl.
*C07C 1/20* (2006.01)
*C07C 2/86* (2006.01)
(Continued)

(52) U.S. Cl.
CPC ............... *C07C 1/22* (2013.01); *B01J 29/084* (2013.01); *B01J 29/40* (2013.01); *B01J 29/7007* (2013.01);
(Continued)

(58) Field of Classification Search
None
See application file for complete search history.

(56) References Cited

U.S. PATENT DOCUMENTS 4,136,128 A * 1/1979 Haag ........................ B01J 29/65
585/467
4,451,356 A   5/1984 Pieters et al.
(Continued)

FOREIGN PATENT DOCUMENTS

WO    WO-2015061802 A1    4/2015
WO    WO-2015061804 A1    4/2015

OTHER PUBLICATIONS

Dickerson, et al.; "Catalytic Fast Pyrolysis: A Review", Energies 2013 (6) pp. 514-538.
(Continued)

*Primary Examiner* — Philip Y Louie
(74) *Attorney, Agent, or Firm* — BakerHostetler

(57) ABSTRACT

Alkylated aromatic products are produced in a process comprising the steps of pyrolysing a pyrolysable raw material in a pyrolysis process to obtain a pyrolysis product stream containing a phenolic product and aromatics products; separating the pyrolysis product stream into a first product stream containing phenolic products and a second product stream containing aromatics products; subjecting the first product stream to a hydrogenation reaction to hydrogenate the phenolic product to obtain an aliphatic alcohol; then reacting the aliphatic alcohol with the aromatics products in the presence of a transalkylation catalyst comprising a solid acid catalyst to form an alkylated aromatic product. The alkylated aromatic product may be subjected to further treatment such as hydroprocessing. The alkylated aromatics product may be used in the production of fuels from biomass.

17 Claims, 1 Drawing Sheet

(51) Int. Cl.
*C07C 1/22* (2006.01)
*C07C 29/20* (2006.01)
*C07G 1/00* (2011.01)
*C10G 1/00* (2006.01)
*C10G 2/00* (2006.01)
*C10G 3/00* (2006.01)
*B01J 29/08* (2006.01)
*B01J 29/40* (2006.01)
*B01J 29/70* (2006.01)

(52) U.S. Cl.
CPC .............. *C07C 2/864* (2013.01); *C07C 29/20* (2013.01); *C07G 1/00* (2013.01); *C10G 1/00* (2013.01); *C10G 2/00* (2013.01); *C10G 3/49* (2013.01); *C07C 2529/08* (2013.01); *C07C 2529/40* (2013.01); *C07C 2601/14* (2017.05); *Y02E 50/32* (2013.01); *Y02P 30/20* (2015.11)

(56) References Cited

U.S. PATENT DOCUMENTS

| | | | |
|---|---|---|---|
| 2012/0238792 A1* | 9/2012 | Watson | B01J 29/126 585/277 |
| 2013/0158329 A1 | 6/2013 | Brandvold | |
| 2013/0338410 A1 | 12/2013 | Wang et al. | |
| 2014/0206909 A1* | 7/2014 | Calaresu | C07C 2/864 568/798 |
| 2016/0024392 A1 | 1/2016 | Keusenkothen | |
| 2016/0289569 A1 | 10/2016 | Baird | |
| 2016/0326438 A1* | 11/2016 | Sorensen | C10B 53/02 |

OTHER PUBLICATIONS

Mukarakate, et al.; "Catalytic Fast Pyrolysis of Biomass: The Reactions of Water and Aromatic Intermediates Produces Phenols", Green Chem., 2015 (17) pp. 4217-4227.

PCT/GB2017/052670, International Search Report dated Nov. 20, 2017.

PCT/GB2017/052670, Written Opinion dated Nov. 20, 2017.

* cited by examiner

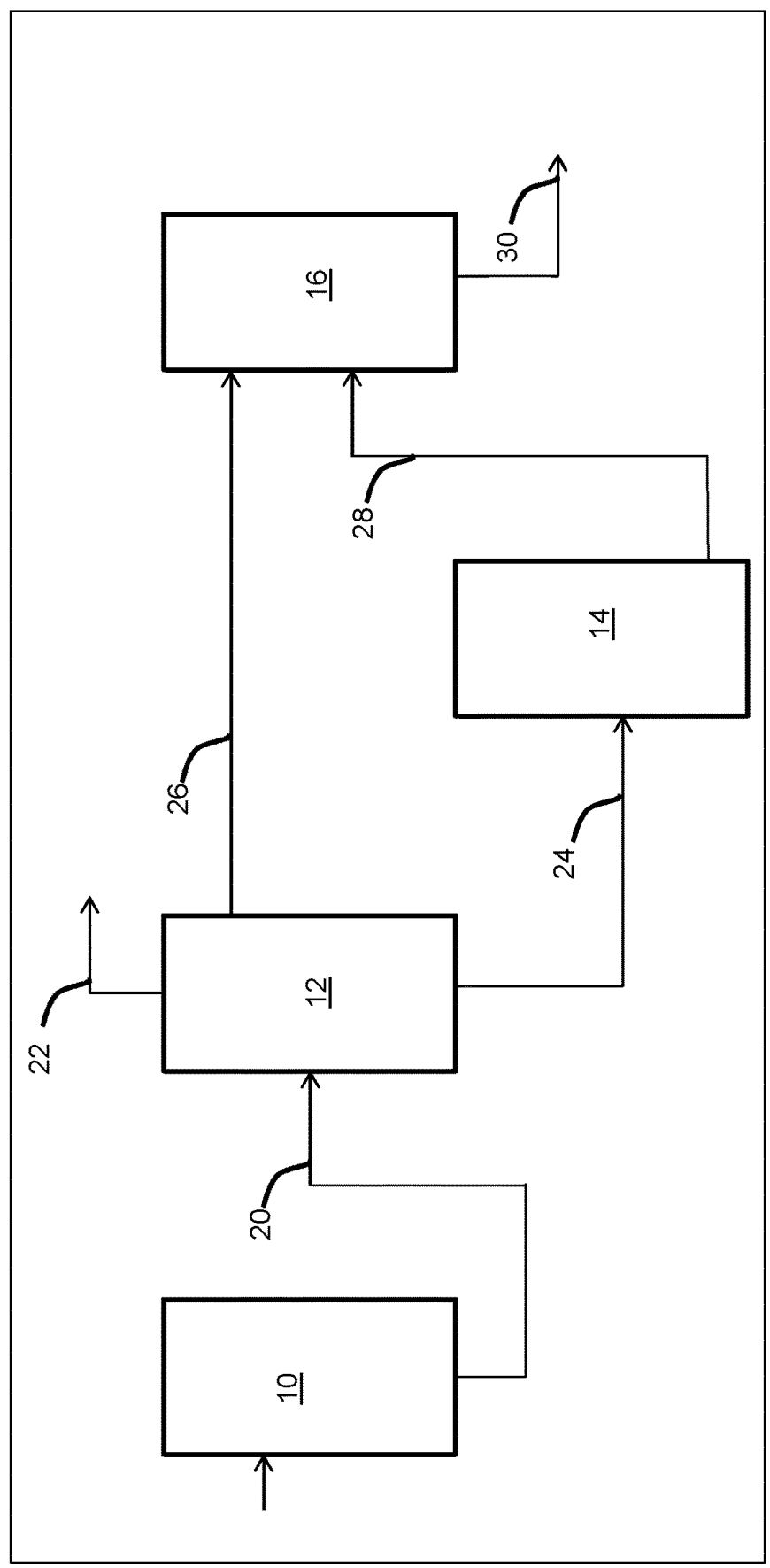

PROCESS FOR THE PRODUCTION OF AN ALKYLATED AROMATIC PRODUCT

CROSS-REFERENCE TO RELATED APPLICATIONS

This application is the National Stage of International Patent Application No. PCT/GB2017/052670, filed Sep. 12, 2017, which claims priority from Great Britain Patent Application No. 1615628.3, filed Sep. 14, 2016, the entire contents of both of which applications are incorporated herein by reference.

The invention concerns a process for the production of hydrocarbons suitable for use in the production of fuels, particularly from bio-derived sources such as wood, via a pyrolysis process.

The use of lignin-containing materials for the production of fuels has typically been carried out by pyrolysis to yield an aromatic-rich product stream of oxygenated and non-oxygenated molecules. This product stream requires further treatment in order to be suitable for the production of fuels because the hydrocarbon chain lengths of the pyrolysis product are typically too short. This problem has been addressed in the prior art. US2013/0338410 describes a method for producing linear alkylbenzene products from a bio-renewable feedstock comprising a mixture of naturally-derived hydrocarbons including separating the mixture of naturally-derived hydrocarbons into a naphtha portion and a distillate portion, reforming the naphtha portion, and using a high purity aromatics recovery process on the reformed naphtha portion to produce benzene. The method further includes separating a normal paraffins portion from the distillate portion, dehydrogenating the normal paraffins portion to produce mono-olefins and then reacting the benzene and the mono-olefins to produce the linear alkylbenzene product.

It is an object of the invention to provide an alternative process for the production of alkylbenzene products from a bio-renewable feedstock.

According to the invention, a process for the production of an alkylated aromatic product comprises the steps of:
a) pyrolysing a pyrolysable raw material in a pyrolysis process to obtain a pyrolysis product stream containing a phenolic product and aromatics products;
b) separating from said pyrolysis product stream a first product stream containing said phenolic product and a second product stream containing said aromatics products;
c) subjecting said first product stream to a hydrogenation reaction to hydrogenate said phenolic product to obtain an aliphatic alcohol;
d) reacting said aliphatic alcohol with said aromatics products in the presence of a alkylation catalyst comprising a solid acid catalyst to from an alkylated aromatic product.

The pyrolysable raw material is preferably biomass. Biomass may include crops and vegetable material grown for the purpose of producing fuel or which are available as waste products from other industries, such as food, agriculture, animal waste, wood, paper or water treatment. Biomass comprising lignocellulosic material is a preferred raw material. The pyrolysis process is known to the skilled person and has been widely described in the literature and practised. Soria and Dickerson (Energies 2013, 6, 514-538 www.mdpi.com/journal/energies) provide a review of pyrolysis and catalytic fast pyrolysis.

Catalytic fast pyrolysis is a preferred pyrolysis process. The pyrolysis product stream may be produced directly from a pyrolysis process or from a process in which the direct product of a pyrolysis reaction is upgraded, usually by contact with a catalyst. In a particular embodiment the pyrolysis process includes a catalytic pyrolysis reaction in the presence of a zeolite. The zeolite is preferably ZSM-5 or ZSM-11, especially in their hydrogen form. Mukarakate et al (Green Chem., 2015, 17, 4217) describe a process of catalytic fast pyrolysis of biomass over HZSM-5 in the presence of steam which increased the proportion of oxygenated aromatics, particularly phenols, in the product. In addition to phenolic products and aromatics, the pyrolysis product typically comprises olefins, carbonyl compounds (hydroxy-)aldehydes, (hydroxy-)ketones, carboxylic acids, heterocyclic compounds such as furans and pyrans and others. "Catalytic pyrolysis" includes catalytic upgrading, such as catalytic vapour-phase upgrading of the pyrolysis products, for example when the biomass is pyrolysed non-catalytically and the products of the pyrolysis are upgraded using a catalytic upgrading process.

Typically, pyrolysis is carried out at about 400-600° C., under an inert atmosphere at atmospheric pressure or above and in the presence of a diluent such as sand. A short contact time (FCC type) is preferred. Catalytic pyrolysis can be carried out under similar conditions, in the presence of catalyst instead of sand. Suitable catalysts for catalytic pyrolysis include ZSM-5, solid acid, solid base, zeolite, MgO, hydrotalcite, $TiO_2$ and $ZrO_2$. ZSM-5 is preferred because it has been observed to produce higher levels of aromatics and phenolics than other catalysts. The pyrolysis process may be carried out in the presence of steam, which may be added to the process.

The phenolic product may comprise phenol and/or substituted phenols, especially alkylphenols, e.g. cresols. The phenolic product may be a mixture of phenol and substituted phenols. The phenolic product may contain higher aromatics such as naphthols.

The aromatics products may comprise mono aromatics and polycyclic aromatics, such as naphthalenes and anthracenes. The aromatics product may comprise hydrocarbons such as benzene, toluene, xylenes, ethylbenzene and other alkyl benzenes, alkyl naphthalenes etc.

The pyrolysis product stream is separated into a first product stream containing the phenolic product(s) and a second product stream containing the aromatics products. Other products may be separated from the pyrolysis product stream if required. The separation may be achieved conveniently by distillation. The phenolics are typically liquids having significantly higher boiling points than the aromatic hydrocarbons. As an example, the pyrolysis product stream may be distilled on a distillation column producing low-boiling "lights" including olefins and other compounds, a mid-cut of about 80-150° C. to include the aromatic hydrocarbons, forming the second product stream and a high-boiling cut of 180-230° C. to include the phenolic products, forming the first product stream. The first and/or the second product streams may be further treated to remove other organic compounds, water or other impurities before step d).

The first product stream containing the phenolic product is hydrogenated in order to hydrogenate the aromatic ring(s) to produce an aliphatic (cyclic) alcohol or mixture of alcohols. Hydrogenation of aromatics is well-known to the skilled person. The reaction is typically carried out with hydrogen in the presence of a hydrogenation catalyst. Typical hydrogenation catalysts include transition metals, usually dispersed on a catalyst support. Sponge metal catalysts, e.g. sponge nickel, may be used. Suitable transition metal catalysts include Cu, Ni, Co, Pd, Pt, Ru, Rh and Ir. Typical supports include $SiO_2$, $Al_2O_3$, $TiO_2$, $ZrO_2$, carbon and SiC. An acid-resistant support may be used, such as modified alumina, alpha alumina, titania, silica, or a silica-alumina. Preferred supports have low acidity, such as, for example modified alumina (titania- or silica-modified), alpha alumina, titania, silica. Hydrogenation is carried out at a suitable temperature, e.g. from 100-400° C., at moderate super-atmospheric pressure, in the liquid phase or the gas phase, usually over a fixed catalyst bed, although other reactor types may be used. The desired product of the hydrogenation reaction is an aliphatic or cyclo-aliphatic alcohol. It is therefore important to select hydrogenation conditions which maximise the potential yield of alcohol, thus avoiding deoxygenation. Hydrogenation temperatures ≤200° C., e.g. from 100 to 200° C. may be preferred in order to avoid deoxygenation of the alcohol.

The aliphatic alcohol obtained in step (c) may comprise more than one different alcohol. The alcohol is preferably a saturated alcohol. The alcohol comprises at least one linear branched or cyclic alcohol which is the product of the hydrogenation of the phenolic product obtained in the pyrolysis step. As the skilled person will be aware, the hydrogenation of a phenolic product may produce non-cyclic alcoholic products if the conditions used lead to the opening of the ring. Additional alcohols, i.e. alcohols which are not derived from the phenolic product of the pyrolysis carried out in step (a) may be added to the alkylation reaction of step (d). The additional alcohol is preferably a saturated alcohol. The additional alcohol may be linear, branched or cyclic. The alcohol is preferably a secondary alcohol. Primary alcohols may be useful in the process but are less preferred due to a tendency to form ethers in the reaction. Tertiary alcohols may be useful in the process but may be less reactive due to steric hindrance. The alcohol fed to the alkylation reaction of step (d) may be C1-C30 (or higher) alcohol, especially C1-C12 alcohol but usually includes at least one C6 cyclohexyl alcohol. An additional alcohol may be derived from a biomass source. Bio-ethanol may be used, particularly as an additional alcohol. An additional alcohol may be derived from an aromatic alcohol which has been produced by pyrolysis of biomass. An additional alcohol may be derived from an aromatic alcohol which has been added to the hydrogenation reaction feed which is hydrogenated in step (c) of the process.

The catalyst comprises a solid acid catalyst. Suitable solid acid catalysts include zeolites, sulphated zirconia, supported heteropolyacids such as supported tungstic acid, supported on supports such as silica, titania, alumina or another standard support. A preferred solid acid catalyst comprises a zeolite. Preferred zeolites have at least 1-dimensional pores (or channels or windows) comprising 10-membered rings or larger. More preferably, the zeolite has 2-dimensional pores in which the pores (or channels or windows) are equal to or greater than 10-membered rings. Even more preferably, the zeolite has 3-dimensional pores in which the pores (or channels or windows) are equal to or greater than 10-membered rings. Most preferably the zeolite has 3-dimensional pores in which the pores (or channels or windows) are equal to or larger than 12-membered rings. We have found that zeolites having pores (or channels or windows) larger than 10-membered rings (approximately 0.5 nm in diameter) are able to promote polyalkylation, especially dialkylated products, leading to a higher fuel value product. Preferred zeolites include zeolite Y and beta-zeolite. Zeolite Y has been found to produce high yields of coupled products and to deactivate more slowly than other zeolites such as ZSM-5 and Ferrierite. The catalyst may be in the form of a powder, granule or shaped unit. Shaped units include tablets, extrudates, spheres, rings etc. Shapes may include cylinders, lobed cylinders, pellets, stars, rings, wheels etc. Shaped units may be formed by methods such as extrusion, tabletting, granulation, moulding, coating, 3-D printing or other method. The catalyst may contain other ingredients in addition to the solid acid. Such other ingredients include diluents, supports, binders, lubricants, pore-formers.

The alkylation catalyst does not comprise a metal which is catalytically active for hydrogenation of aromatic rings. Therefore, in a preferred embodiment, the catalyst is essentially free of palladium, platinum, rhodium, cobalt, nickel, copper, ruthenium and iridium.

The feed stream for the alkylation reaction of step (d) comprises an aromatic compound derived from the pyrolysis reaction of step (a) and an alcohol derived from the hydrogenation reaction of step (c). The feed stream may comprise more than one different aromatic compound. The aromatic compound may be substituted or unsubstituted. The aromatic compound typically comprises hydrocarbons (e.g. toluene) and oxygenated hydrocarbons, such as alcohols (e.g. cresol) or ethers, (e.g anisole) etc. The aromatic compound may comprise compounds selected from the group consisting of hydrocarbons, oxygenated hydrocarbons, and mixtures of hydrocarbons and oxygenated hydrocarbons. At least 90% by weight of the aromatic compounds in the feed stream for the alkylation reaction of step (d) may consist of compounds selected from the group consisting of hydrocarbons and oxygenated hydrocarbons.

The feed stream for the alkylation reaction in step (d) may consist of or consist essentially of a hydrogenated phenolics product stream (such as the aliphatic alcohol obtained in step (c)) and an aromatics product stream (such as the aromatics product stream derived in step (b)), optionally with additional alcohol and further optionally in the presence of a diluent or solvent. The feed stream may contain water, for example up to about 50 wt % when a biomass feed is used. A suitable diluent or solvent may be selected by the skilled person. A hydrocarbon, especially an alkane such as a C6-C20 alkane may be used as a diluent or solvent for the reactants.

The alkylation reaction may be carried out as a liquid-phase reaction or a gas-phase reaction. The reactions may be carried out in a continuous or a batch reactor. Suitable reactors may be selected by the skilled person, for example a fixed bed trickle flow reactor is suitable for carrying out the reaction in liquid phase. The reactor preferably has means for temperature control and heating or cooling means. The reaction may be carried out in the presence of an inert gas such as nitrogen. We have found that hydrogen is essentially inert in the present reaction, in the absence of a hydrogenation catalyst. The reaction may be carried out in the presence or absence of hydrogen. It is a particular benefit of the process of the invention that hydrogen is not required for the reaction. The reaction pressure may be in the range from about 0.1 to about 10 MPa, e.g. 0.5-5 MPa. The reaction is carried out at a suitable temperature. A suitable temperature range for the reaction is 100-400° C., preferably 150-300° C., especially 180-260° C.

The hydrogenation reaction may be carried out as a liquid-phase reaction or a gas-phase reaction. Sufficient hydrogen is fed to the reactor to effect the hydrogenation of the phenolic products obtained from the pyrolysis step. The reactions may be carried out in a continuous or a batch reactor. Suitable reactors may be selected by the skilled person, for example a fixed bed trickle flow reactor is suitable. The reactor preferably has means for temperature control and heating or cooling means. The reaction may be carried out in the presence of an inert gas such as nitrogen. The reaction pressure may be in the range from about 0.1 to about 10 MPa, e.g. 0.5-5 MPa. The reaction is carried out at a suitable temperature. A suitable temperature range for the hydrogenation reaction is 200° C., e.g. from 100 to 200° C. may be preferred in order to avoid deoxygenation of the alcohol or dehydration The alkylated aromatic product formed in step (d) typically comprises a mixture of aromatic compounds. The alkylated aromatic product may comprise an alkylbenzene, especially cyclohexylbenzene. Other products may be formed in the alkylation reaction, depending on the composition of the first and second product streams and on whether cracking or other reactions occur under the conditions of the process. The alkylated aromatic product may be mono-, di- or tri-alkylated. The alkylated aromatic product formed in step (d) by the alkylation reaction may be used as a fuel or further processed. Further processing of the alkylated aromatic product may include hydroprocessing or hydrogenation, for example hydrogenation of the aromatic portion of the products. Further processing of the alkylated aromatic product may include hydrodeoxygenation to remove residual oxygen/oxygenated substituents from the products. Typically, hydrodeoxygenation takes place at a temperature range from about 100 to about 400° C. over a catalyst system including a hydrogenation catalyst and a solid acid catalyst. Examples of suitable catalyst systems include catalysts containing molybdenum, such as CoMo and NiMo catalysts. The hydrodeoxygenation may take place in a trickle bed reactor, the alkylated aromatic product being contacted with flowing hydrogen.

An example of a simplified schematic process flowsheet is shown in the FIGURE. Biomass is subjected to a catalytic fast pyrolysis (CFP) reaction in a CFP reactor 10. A product stream 20 is separated in a distillation column 12 in lights 22, phenolic compounds 24 and other aromatics 26. The phenolic products are hydrogenated in reactor 24 containing a nickel hydrogenation catalyst. The hydrogenated alcohols are then reacted with the aromatics products in alkylation reactor 16, containing a zeolite catalyst. The alkylated aromatics are then removed via line 30 for hydroprocessing and hydrodeoxygenation.

The invention claimed is:

1. A process for the production of an alkylated aromatic product comprising the steps of:
   a. pyrolysing a pyrolysable raw material comprising lignocellulosic biomass in a pyrolysis process to obtain a pyrolysis product stream containing a phenolic product comprising phenol or a substituted phenol and aromatics products;
   b. separating from said pyrolysis product stream a first product stream containing said phenolic product and a second product stream containing said aromatics products;
   c. subjecting said first product stream to a hydrogenation reaction to hydrogenate said phenolic product to obtain an aliphatic alcohol;
   d. reacting said aliphatic alcohol with said second product stream in the presence of a alkylation catalyst comprising a solid acid catalyst to form an alkylated aromatic product.

2. The process of claim 1, wherein the pyrolysis process is a catalytic pyrolysis process.

3. The process of claim 2, wherein said catalytic pyrolysis process is carried out in the presence of a catalyst comprising ZSM-5 or ZSM-11.

4. The process of claim 1, wherein the separation of the pyrolysis product stream comprises a distillation step.

5. The process of claim 1, wherein the phenolic product is hydrogenated with hydrogen in the presence of a catalyst comprising a transition metal.

6. The process of claim 1, wherein the aliphatic alcohol comprises a mixture of alcohol compounds.

7. The process of claim 1, wherein additional alcohols are added to the alkylation reaction of step (d).

8. The process of claim 1, wherein the solid acid catalyst is selected from the group consisting of zeolites, sulphated zirconia and supported heteropolyacids.

9. The process of claim 4, wherein the solid acid catalyst comprises a zeolite.

10. The process of claim 9, wherein the solid acid catalyst comprises a zeolite having at least 1-dimensional pores, channels or windows comprising 10-membered rings or larger.

11. The process of claim 10, wherein the zeolite has at least 2-dimensional pores in which the pores, channels or windows are equal to or greater than 10-membered rings.

12. The process of claim 11, wherein the zeolite has 3-dimensional pores in which the pores, channels or windows are equal to or greater than 10-membered rings.

13. The process of claim 12, wherein the zeolite has 3-dimensional pores in which the pores, channels or windows are equal to or larger than 12-membered rings.

14. The process of claim 9, wherein the zeolite comprises zeolite Y or BEA.

15. The process of claim 1, wherein the alkylation catalyst does not comprise a metal that is catalytically active for hydrogenation of aromatic rings.

16. The process of claim 1, wherein said alkylated aromatic product comprises an alkylbenzene.

17. The process of claim 1, wherein the alkylated aromatic product is mono-, di- or tri-alkylated.

* * * * *